US006916314B2

(12) United States Patent
Schneider et al.

(10) Patent No.: US 6,916,314 B2
(45) Date of Patent: Jul. 12, 2005

(54) MEDICAL INSTRUMENT WITH REMOVABLE TOOL

(75) Inventors: Martin Schneider, Denkingen (DE); Uwe Bacher, Tuttlingen (DE)

(73) Assignee: Karl Storz GmbH & Co. KG (DE)

( * ) Notice: Subject to any disclaimer, the term of this patent is extended or adjusted under 35 U.S.C. 154(b) by 146 days.

(21) Appl. No.: 10/354,523

(22) Filed: Jan. 30, 2003

(65) Prior Publication Data

US 2003/0120272 A1 Jun. 26, 2003

Related U.S. Application Data

(63) Continuation of application No. PCT/EP01/08696, filed on Jul. 27, 2001.

(30) Foreign Application Priority Data

Aug. 3, 2000 (DE) .......................................... 100 38 576

(51) Int. Cl.[7] .............................................. A61B 17/00
(52) U.S. Cl. ............................... 606/1; 606/46; 606/41
(58) Field of Search ................................ 606/1, 45–52, 606/170, 205–207

(56) References Cited

U.S. PATENT DOCUMENTS

| 5,195,958 | A | * | 3/1993 | Phillips ....................... 604/33 |
| 5,334,198 | A | * | 8/1994 | Hart et al. ..................... 606/52 |
| 5,480,409 | A | * | 1/1996 | Riza ............................ 606/205 |
| 5,489,290 | A | | 2/1996 | Furnish ....................... 606/170 |
| 5,499,998 | A | * | 3/1996 | Meade ........................ 606/207 |
| 5,571,137 | A | | 11/1996 | Marlow et al. ............. 606/207 |
| 5,593,402 | A | | 1/1997 | Patrick ........................... 606/1 |
| 5,618,303 | A | | 4/1997 | Marlow et al. ............. 606/205 |
| 5,722,988 | A | | 3/1998 | Weisshaupt ................. 606/205 |
| 5,766,184 | A | | 6/1998 | Matsuno et al. ............ 606/142 |
| 5,769,841 | A | * | 6/1998 | Odell et al. ..................... 606/1 |

FOREIGN PATENT DOCUMENTS

| CH | 293 302 | | 9/1953 |
| DE | 25 19 827 | | 2/1978 |
| DE | G 93 17 535.3 | U1 | 3/1994 |
| DE | 43 23 584 | A1 | 1/1995 |
| DE | 43 41 735 | C1 | 8/1995 |
| DE | 43 23 584 | A1 | 10/1995 |
| DE | 44 96 959 | T1 | 9/1996 |
| DE | 693 10 037 | T2 | 9/1997 |
| DE | 694 17 361 | T2 | 7/1999 |
| DE | 198 15 228 | C1 | 10/1999 |
| DE | 198 15 228 | * | 10/1999 |
| DE | 198 54 313 | A1 | 6/2000 |
| DE | 100 38 576 | C1 | 5/2002 |
| DE | 100 38 576 | C1 | 6/2002 |
| EP | 0 217 559 | B1 | 5/1986 |
| EP | 0 217 559 | B1 | 9/1986 |
| EP | 0 738 501 | A1 | 10/1996 |

(Continued)

*Primary Examiner*—Michael Peffley
(74) *Attorney, Agent, or Firm*—St. Onge Steward Johnston & Reens LLC

(57) ABSTRACT

A medical instrument has a shaft and a tool which is mounted on a distal end of the shaft in such a way as to be removable therefrom. The shaft has an inner shaft and a tubular shaft which surrounds the inner shaft and which is longitudinally displaceable relative thereto. The tool is locked on the shaft when the tubular shaft is in a locking position pushed forward relative to the inner shaft, and it can be removed from the shaft when the tubular shaft is in a release position pulled back relative to the inner shaft. For easier handling of the instrument when changing the tool, it is proposed that the instrument has an actuating element which is movable substantially transversely with respect to the longitudinal direction of the tubular shaft and which is connected operatively to the tubular shaft in such a way that the tubular shaft is moved from the locking position to the release position by moving the actuating element from a first position to a second position, and vice versa.

21 Claims, 5 Drawing Sheets

FOREIGN PATENT DOCUMENTS

| | | |
|---|---|---|
| EP | 0 577 423 B2 | 1/2001 |
| EP | 0 577 423 B2 | 11/2001 |
| WO | WO 94/27511 | 2/1994 |
| WO | WO 94/27511 | 12/1994 |
| WO | WO 95/07662 | 3/1995 |
| WO | WO 96/24298 | 2/1996 |
| WO | WO 96/24298 | 8/1996 |

* cited by examiner

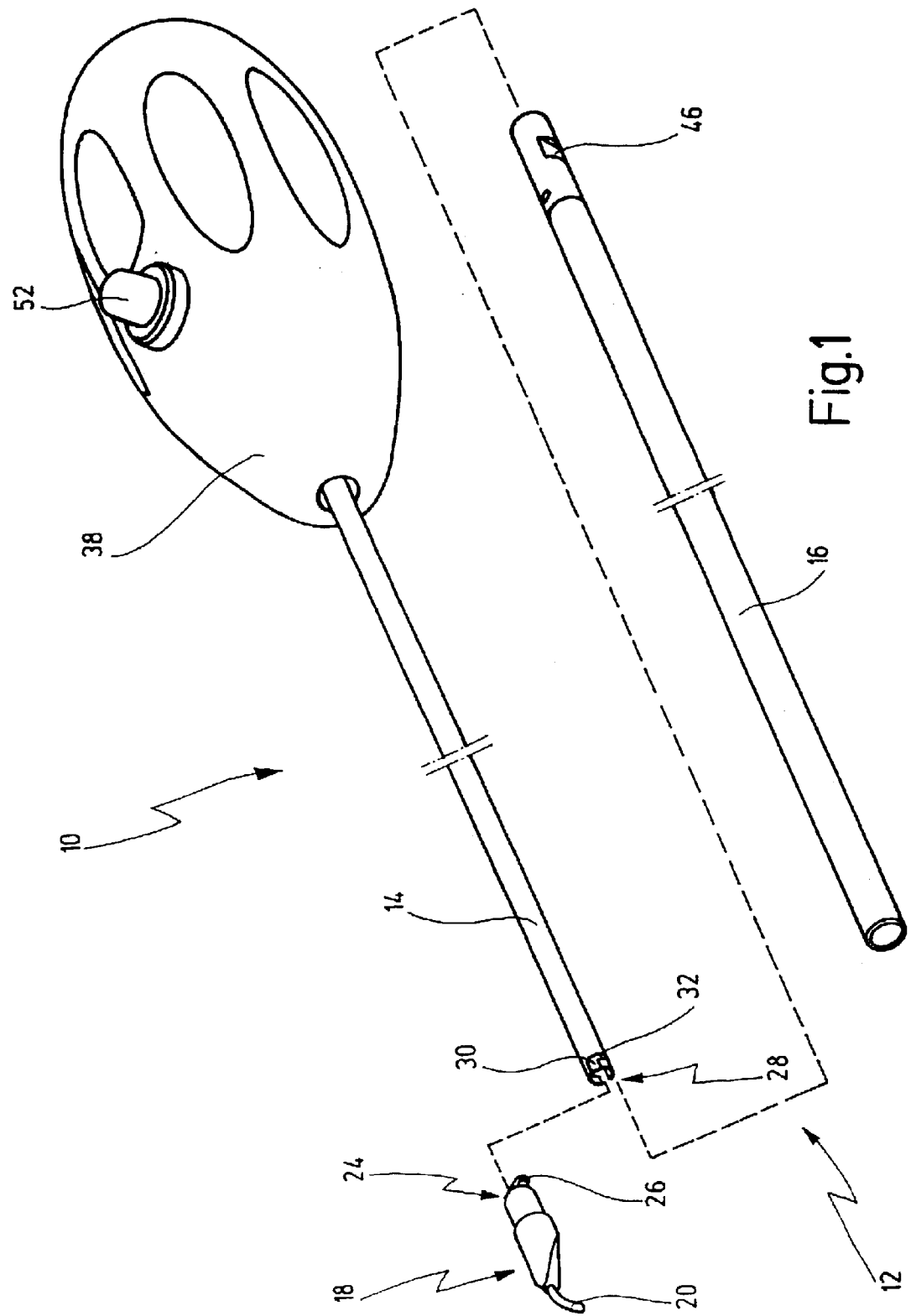

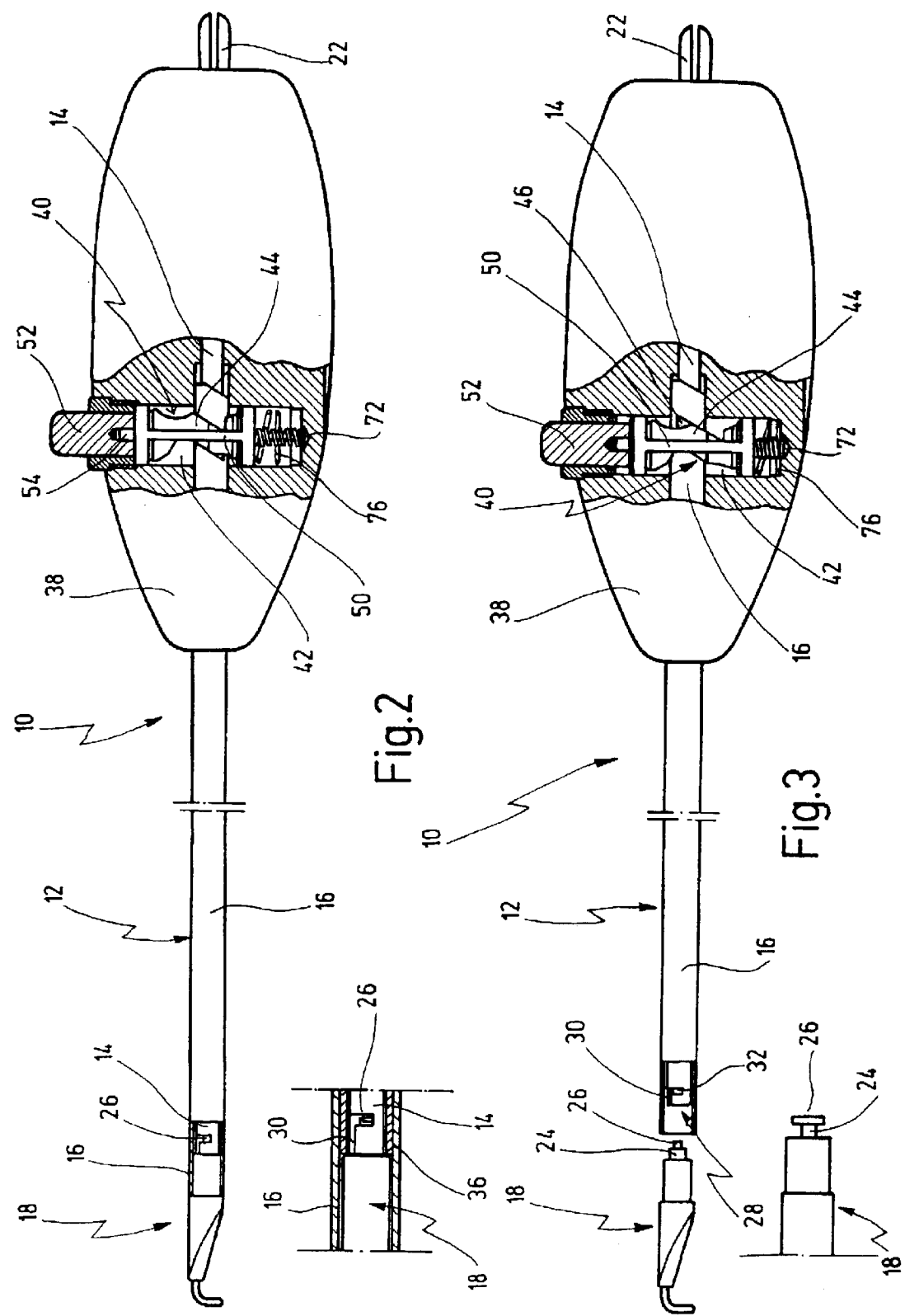

MEDICAL INSTRUMENT WITH REMOVABLE TOOL

CROSS REFERENCE TO PENDING APPLICATIONS

This application is a continuation of pending international patent application PCT/EP01/08696 filed on Jul. 27, 2001 which designates the United States and claims priority of German patent application DE 100 38 576.1 filed on Aug. 3, 2000.

BACKGROUND OF THE INVENTION

The invention relates to a medical instrument, comprising a shaft, and a tool which is mounted on a distal end of the shaft in such a way as to be removable therefrom, the shaft having an inner shaft and a tubular shaft which surrounds the inner shaft and which is longitudinally displaceable relative thereto, the tool being locked on the shaft when the tubular shaft is in a locking position and being removable from the shaft when the tubular shaft is in a release position.

Such an instrument is known from DE-C-198 15 228.

An instrument of the type mentioned at the outset is used for surgical interventions on the human or animal body, in particular in the context of minimally invasive surgery.

Depending on the function and design of the tool arranged at the distal end of the shaft, the instrument can be a cutting instrument, a gripping instrument and/or a coagulating instrument, to mention some examples. In the case of a cutting instrument, the tool can be designed as a blade or in the form of two jaw parts which interact to cut in the manner of scissors. In the case of a coagulating instrument, the tool can be designed as an electrode which can be acted upon with high-frequency current from the proximal end of the instrument. The present invention can be used with all the aforementioned instrument types and also with other instrument types, such as needle holders.

Whereas the tool in conventional instruments was connected securely to the distal end of the shaft and could be removed from the shaft for cleaning purposes only by completely disassembling the instrument, the aforementioned DE-C-198 15 228 discloses an instrument in which the tool at the distal end of the shaft can be removed without the instrument having to be disassembled for this purpose.

In this known instrument, the tool is an electrode tip for cutting and coagulating tissues by means of high-frequency current. The electrode tip is held exchangeably on the shaft, said shaft having an inner shaft and a tubular shaft which surrounds the inner shaft and which is longitudinally displaceable relative to the inner shaft. The electrode tip is held on the inner shaft, said inner shaft having fixing portions which can be moved radially outward and which release the electrode tip holder inserted into the inner shaft in its outwardly moved release position, and, by contrast, fix it axially in an inwardly moved locking position. The tubular shaft covers the fixing portions in a pushed-forward locking position and releases the fixing portions in a retracted release position.

A comparable instrument with a removable tool at the distal end of the shaft is known from DE-C-43 41 735, this known instrument having, as its tool, two jaw parts which can move relative to one another and which can be actuated, via a power transmission element, by means of a handle at the proximal end of the shaft. The power transmission element in this case extends right through the inner shaft. A design of the medical instrument mentioned at the outset with a power transmission element movable longitudinally in the inner shaft for moving the tool is also possible in the context of the present invention.

The advantage of a medical instrument with a removable tool lies in the fact that different tools can be interchanged during an operation performed with the instrument. In this way, it is no longer necessary to have several complete instruments ready to hand, but only different tools, which can then be interchanged as desired. In the case where the tool is an electrode, it is possible for example to use different tools with different electrode shapes. Such an instrument can thus be used in a more universal manner compared to conventional instruments.

In order to gain acceptance for a medical instrument in which the tool can be removed from the shaft and can be replaced with other tools, in contrast to conventional instruments which have no removable tool, it is necessary to ensure that the handling of the instrument when changing the tool is simple and that the tool change can be done quickly and efficiently.

In the instrument known from DE-C-198 15 228 mentioned above, it has been proposed to simplify handling by designing the tubular shaft so that, in the pushed-forward locking position, it can be rotated about the longitudinal axis of the inner shaft into a position in which it is fixed in the longitudinal direction by a bayonet-like lock on the inner shaft. To remove the tool from the distal end of the shaft, the tubular shaft must be pulled back by hand by means of two grip parts, one of which is connected to the tubular shaft, being turned about the longitudinal axis of the inner shaft in such a way that a pin of the bayonet-like lock engages in a longitudinal groove of the bayonet, after which the tubular shaft can be pulled back by hand.

A disadvantage of this actuating mechanism of the known instrument is that the tubular shaft has to be turned and pulled back relative to the inner shaft by hand. This construction of the actuating mechanism thus requires two-handed operation; one-handed operation is at any rate difficult.

The object of the invention is therefore to develop a medical instrument of the type mentioned at the outset in such a way that the handling involved in removing or applying the tool at the distal end of the shaft is further simplified.

SUMMARY OF THE INVENTION

According to the invention, a medical instrument is provided, comprising: a shaft having an extension in a longitudinal direction, and further having a distal end, said shaft further having an inner shaft and a tubular shaft surrounding said inner shaft and being displaceable relative thereto; a tool mounted on said distal end of said shaft in such a way as to be removable therefrom, said tool being locked on said shaft when said tubular shaft is in a locking position and being removable from said shaft when said tubular shaft is in a release position relative to said inner shaft; and an actuating element movable substantially transversely with respect to said longitudinal direction of said tubular shaft and connected operatively to said tubular shaft in such a way that said tubular shaft is moved from said locking position to said release position by moving said actuating element from a first position to a second position, and vice versa.

In the instrument according to the invention, an actuating mechanism is accordingly provided which comprises an actuating element which can be moved substantially transversely with respect to the longitudinal direction of the tubular shaft. This movable actuating element is in operative connection with the tubular shaft in such a way that the movement of the movable actuating element is converted into a movement of the tubular shaft in the longitudinal direction thereof. The advantage of the actuating element which is movable substantially transversely with respect to the longitudinal direction of the tubular shaft is that such an actuating element, when it is arranged on the hand grip of the instrument, can be easily operated by means of thumb pressure on a push button, for example. Such actuation of the instrument for displacing the tubular shaft from the locking position to the release position provides for one-handed operation of the instrument when changing tool. The tubular shaft can therefore be displaced relative to the inner shaft using the same hand which is also holding the instrument as such, while the other hand can already be used at the same time to handle the tool which is to be removed or the tool which is to be applied.

In a preferred embodiment, the actuating element has an engagement portion which engages with a recess on the tubular shaft and is movable relative to said recess, the engagement portion and the recess having such a configuration that a movement of the actuating element directed substantially transversely with respect to the longitudinal direction is converted into a longitudinal movement of the tubular shaft.

This measure results in the further advantage of a structurally very simple construction of the actuating mechanism. At the same time, this advantageously secures the shaft against rotation. It is also conceivable, however, for the operative connection between the actuating element and the tubular shaft to be realized via a gear mechanism with conical gear wheels.

It is preferable here if the engagement portion and the recess extend obliquely with respect to the longitudinal direction of the shaft and obliquely with respect to the direction of movement of the actuating element.

By means of this measure, a linear actuating mechanism is obtained, i.e. the path of movement of the tubular shaft is proportional to the path of movement of the actuating element. This design proves to be advantageous because the tubular shaft moves uniformly with the movement of the actuating element.

In a further preferred embodiment, the actuating element can be moved from the second position to a third position in which the actuating element completely disengages from the recess, and the tubular shaft can be removed from the inner shaft or can be mounted thereon in the third position.

This measure has the advantage that not only can the actuating element displace the tubular shaft for the purpose of changing the tool, but the actuating element at the same time has the function of an end-stop for the tubular shaft in order to release the tubular shaft from the inner shaft or from the hand grip.

In a further preferred embodiment, the actuating element is prestressed into the first position.

This measure on the one hand has the advantage that, because of the prestressing of the actuating element into the first position, the tubular shaft returns automatically from the release position to the locking position when the actuating element is let go. On the other hand, this measure has the further advantage that the tubular shaft is fixed in the locking position relative to the inner shaft by the prestressing of the actuating element in the locking position.

In a further preferred embodiment, the actuating element can be moved from the first position to the second position counter to a first force and, in order to remove the tubular shaft from the inner shaft, can be moved from the second position to the third position counter to a second force which is greater than the first force.

An advantage in this connection is that a two-stage actuating mechanism is created whose first stage serves for displacing the tubular shaft relative to the inner shaft in order to change the tool at the distal end of the shaft, while the second stage serves for disassembly of the instrument, i.e. for removal of the tubular shaft. In addition, because of the different resistances, the person operating the instrument can tell when the end of the first movement stage is reached, that is to say when, upon further movement of the actuating element, the resistance increases in a stage-like manner. In this way, when changing a tool, the person can avoid pushing the actuating element through to the third position in which the tubular shaft can be removed from the instrument.

In this connection it is preferred, in order to fit the tubular shaft on the inner shaft, if the actuating element can be moved into the third position counter to the first force alone.

In connection with the aforementioned embodiment, this measure has the advantage that the actuating element has to be moved from the second position to the third position counter to a greater force only for the purpose of removing the tubular shaft from the inner shaft, which in each case ensures that, when changing the tool, the actuating element is not moved into the third position, i.e. into the release position for removal of the tubular shaft. Since, when fitting the tubular shaft on the inner shaft, the aforementioned safety aspect does not have to be considered, the aforementioned measure also simplifies the handling of the instrument according to the invention when fitting the tubular shaft on the inner shaft, because only the first force has to be overcome in order to fit the tubular shaft on the inner shaft.

In a further preferred embodiment, the actuating element has two engagement portions which engage, at opposite circumferential positions of the tubular shaft, in corresponding recesses.

By means of this measure, the actuating mechanism is improved still further in terms of its operational safety because the actuating element with the two engagement portions at opposite circumferential positions engages symmetrically on the tubular shaft, as a result of which a tilting or jamming of the actuating element with the shaft is avoided.

In a further preferred embodiment, the actuating element has an opening which adjoins the engagement portion and whose clear diameter is greater than the external diameter of the tubular shaft.

This measure is of advantage in particular in connection with the previous measure, according to which the actuating element has two engagement portions, so that the actuating element can then as a whole have a passage in the shape of a keyhole. In the third position of the actuating element, the opening surrounds the tubular shaft concentrically, so that the tubular shaft can then be pulled with its proximal portion out from the actuating element through the opening.

In a further preferred embodiment, the actuating element is supported against a first spring.

This measure has the advantage of a structurally simple configuration for prestressing the actuating element into the first position, the actuating element being able to be moved from the first position to the second position counter to the force of the first spring.

In this connection, it is further preferred if the actuating element is guided in a guide element which is connected to an operating element, for example in the form of a push button, in such a way that, by pressing the operating element, the guide element entrains the actuating element.

This measure is advantageous in particular if, according to a further preferred embodiment, the actuating element is displaceable relative to the guide element.

This embodiment has the advantage that the actuating element can be moved when uncoupled from the operating element and independently of the operating element. This is advantageous in particular for easier fitting of the tubular shaft in order, according to an aforementioned embodiment, to move the actuating element into the third position counter to the first, lower force alone, when in fact the second counterforce is acting on the guide element.

In a further preferred embodiment, the actuating element, additionally supported against a second spring, can be moved directly or indirectly from the second position to the third position.

The provision of a second spring in addition to the first spring represents a structurally advantageous and simple configuration for ensuring that the actuating element can be moved from the first position to the second position counter to a first force and from the second position to the third position only counter to a higher, second force.

In a further preferred embodiment, the second spring is supported against the guide element and only upon movement of the actuating element from the second position to the third position is it made active for removing the tubular shaft.

With this measure, the above-described two-stage actuating mechanism for the actuating element is created in a structurally simple way.

In this connection, it is further preferred if the clear internal diameter of the second spring is greater than the external circumference of the actuating element, the first spring being arranged inside the second spring.

This measure affords the advantage that, in order to fit the tubular shaft on the instrument, and as a result of the aforementioned embodiment, the actuating element too can be moved into the third position counter to the force of the first spring alone, by which means the fitting of the tubular shaft is made easier.

In a further preferred embodiment, the second spring is harder than the first spring.

If the second spring is harder than the first spring, the transition of the actuating element from the first movement stage to the second movement stage is easier still for the person using the instrument to detect, because in this way a kind of limit stop for the end of the first movement stage is created, with the second, harder spring becoming operative starting from the second position.

In a further preferred embodiment, an abutment bevel for the proximal end of the tubular shaft is formed on the distal side of the actuating element, so that the actuating element is moved into the third position when the proximal end runs onto the abutment bevel.

This measure has the advantage that it is possible to fit the tubular shaft on the inner shaft without actuating the operating element, simply by pushing the tubular shaft in a particularly simple manner onto the inner shaft. Particularly in connection with the aforementioned embodiment, the proximal end of the tubular shaft in this case moves the actuating element into the third position only counter to the first, lower force alone. The tubular shaft is then pushed in the proximal direction until the recess on the tubular shaft comes to lie level with the engagement portion of the actuating element, in which position the actuating element, with suitable spring prestressing, as mentioned previously, springs automatically into the first position and the engagement portion engages in the recess on the tubular shaft. In this way, an advantageously easy-to-use latching mechanism is created for fitting the tubular shaft on the inner shaft.

In a further preferred embodiment, the actuating element is arranged to be operated on a hand grip of the instrument.

In this way, when changing the tool or removing the tubular shaft, the actuating element in conjunction with an operating element, such as a push button, can be particularly easily operated using the same hand which is also holding the hand grip.

In a further preferred embodiment, a distal end of the inner shaft has a bayonet-like recess with a portion which initially extends axially and then about the circumference, a holder being arranged at the proximal end of the tool, which holder can be inserted with a transversely extending portion into the bayonet-like recess, and at least one axial recess being formed on the tubular shaft, into which recess the transversely extending portion of the holder engages in the locking position of the tubular shaft.

Whereas the instrument known from DE-C-198 15 228 has a holder like a collet chuck for the tool with radially movable parts, this embodiment has the advantage that it is possible to dispense with movable parts which have the disadvantage that they risk being broken, especially when, as in the known instrument, they are designed as elastic tongues.

It is further preferable if the tubular shaft is pushed forward relative to the inner shaft in the locking position and is pulled back in the release position, because the aforementioned bayonet lock in particular can then be designed with a simple construction.

In a preferred embodiment of the instrument according to the invention, the tool is an electrode for coagulation or cutting of tissue.

While this represents a preferred embodiment of the instrument according to the invention, the invention however is not restricted to an HF instrument of this type, and it can also be advantageously used with other instruments.

Further features and advantages will become clear from the following description and from the attached drawing.

It goes without saying that the features mentioned above and the features yet to be explained below can be used not only in the respectively stated combination but also in other combinations or in isolation, without departing from the scope of the present invention.

BRIEF DESCRIPTION OF THE DRAWINGS

An illustrative embodiment of the invention is shown in the drawing and is discussed in more detail in the description below. In the drawing:

FIG. 1 shows a perspective overall view of a medical instrument, with tool removed and tubular shaft removed;

FIG. 2 shows the instrument from FIG. 1 in a side view in the assembled state, with partial cutaways, and with a detail being shown on a larger scale in a separate part of the figure;

FIG. 3 shows the instrument from FIGS. 1 and 2 in an operating position in which the tool can be removed or mounted, with a detail being shown on a larger scale in a separate part of the figure;

DETAILED DESCRIPTION OF A PREFERRED EMBODIMENT

A medical instrument labeled with the general reference number 10 is shown in FIGS. 1 to 4.

The instrument 10 is an instrument for coagulation or cutting of tissue by means of high-frequency current.

Figure 4:
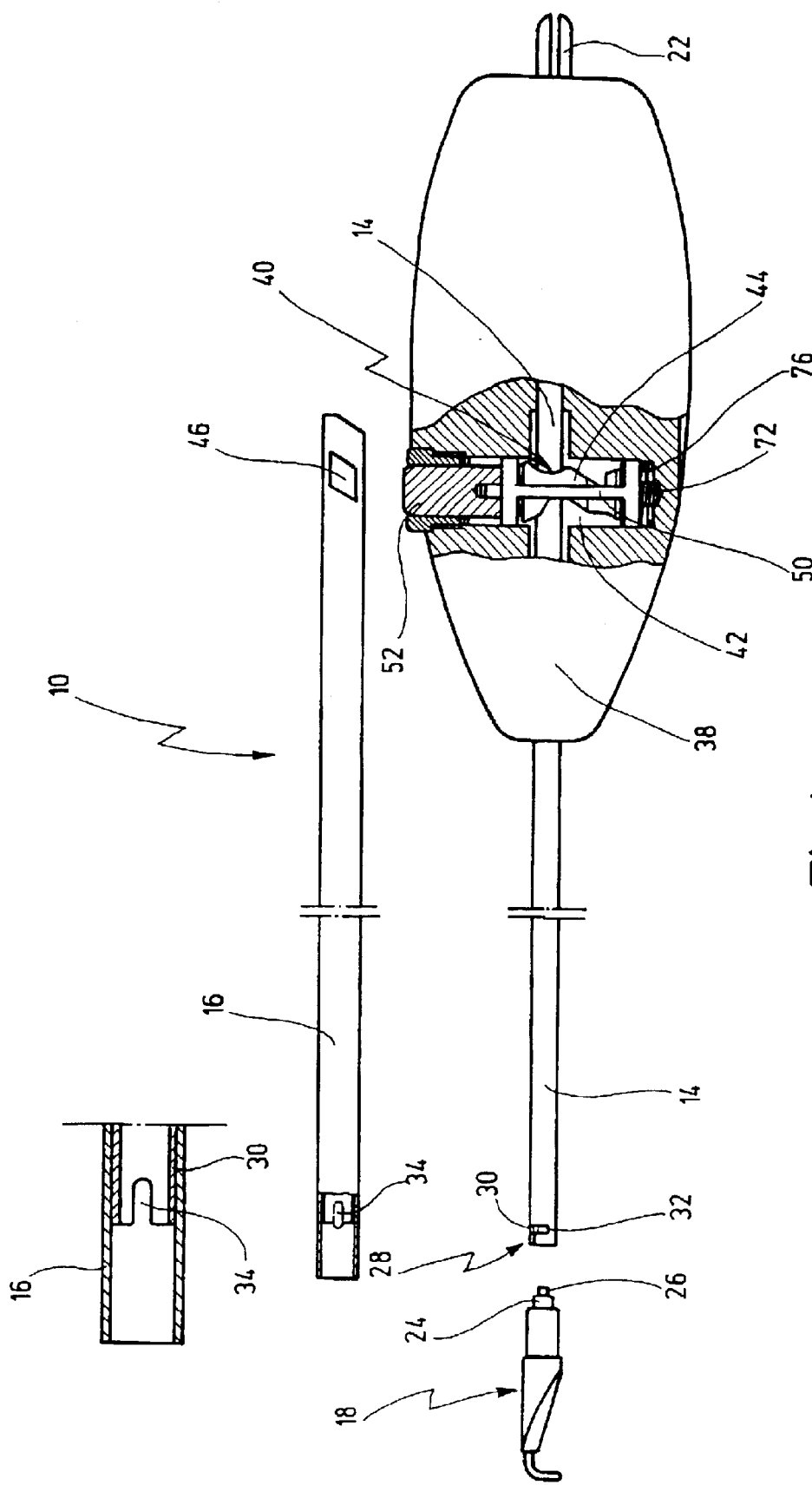
FIG. 4 shows the instrument from FIGS. 1 to 3 in an operating position in which the tubular shaft can be removed or mounted, with a detail being shown on a larger scale in a separate part of the figure.

In FIG. 1, the instrument 10 is shown in a perspective view and divided up into its main structural parts. The instrument 10 has a shaft 12 which comprises an inner shaft 14 and a tubular shaft 16 surrounding the inner shaft 14. In FIGS. 1 and 4, the tubular shaft 16 is shown removed from the inner shaft 14. In FIGS. 2 and 3, the tubular shaft 16 is fitted on the inner shaft 14.

A tool 18 is mounted on the distal end of the shaft 12 in such a way as to be removable therefrom. In FIGS. 1, 3 and 4, the tool 18 is shown removed from the shaft 12, and in FIG. 2 it is shown mounted on the shaft 12.

In accordance with the embodiment of the instrument 10 as an instrument for coagulation or cutting of tissue by means of high-frequency current, the tool 18 has an electrode tip 20.

The inner shaft 14 serves to deliver current to the electrode tip 20, the inner shaft 14 extending as far as the proximal end of the instrument 10 and being connected electrically conductively there to a contact 22 to which a high-frequency plug (not shown) connected to a high-frequency current source (not shown) can be connected.

To mount the tool 18 on the shaft 12 in such a way as to be removable therefrom, the tool 18 has at its proximal end a holder 24 which, in FIG. 3, is shown in a plan view in an enlarged detail of the proximal end of the tool 18. At its outermost proximal end, the holder 24 has a transversely extending portion 26 which is designed in the shape of a T.

The distal end of the inner shaft 14 has a bayonet-like recess 28 which has an axial portion 30 extending in the proximal direction from the outermost distal end of the inner shaft 14 and, adjoining this portion 30, a portion 32 extending partially about the circumference. To be more exact, the bayonet-like recess at the distal end of the inner shaft 14 has two axially extending portions 30 lying opposite each other, and two circumferential portions 32 lying diametrically opposite each other.

The holder 24 of the tool 18 can be inserted with its transversely extending portion 26 into the bayonet-like recess 28, i.e. first into the axially extending portions 30 and, by turning approximately 90° about its longitudinal axis in the clockwise direction (viewed from the distal end), into the circumferentially extending portions 32 of the bayonet-like recess 28.

To secure the tool 18 on the shaft 12, the tubular shaft 16 has, in the area of its distal end, an axial recess 34 which is shaped as an oblong hole and into which the transversely extending portion 26 of the holder 24 of the tool 18 engages. The recess 34 is in this case provided in a sleeve 36 which is arranged in the tubular shaft 16, in the area of its distal end. By providing the sleeve 36 inside the tubular shaft 16, the tubular shaft 16 can have a continuously closed outer wall. The transversely extending portion 26 of the holder 24 has a transverse dimension corresponding approximately to the internal diameter of the distal end of the tubular shaft 16, on the distal side of the sleeve 36, and approximately to the external diameter of the sleeve 36.

The tubular shaft 16 is longitudinally displaceable relative to the inner shaft 14, the tool 18 being locked on the shaft when the tubular shaft 16 is in a locking position pushed forward relative to the inner shaft 14, as is shown in FIG. 2, the transversely extending portion 26 of the holder 24 engaging in the recess 34 of the tubular shaft 16 in this locking position of said tubular shaft 16.

In a release position of the tubular shaft 16, shown in FIG. 3, in which it is pulled back relative to the inner shaft 14, the tool 18 can by contrast be removed from the shaft 12 because the transversely extending portion 26 of the holder 24 of the tool 18 then no longer engages in the recess 34 of the tubular shaft 16, and it can thus be removed from the bayonet-like recess 28 of the inner shaft 14, first by turning it through approximately 90° counterclockwise and finally by pulling it out from the axially extending portion 30 of the bayonet-like recess 28.

In order to move the tubular shaft 16 from the pushed-forward locking position shown in FIG. 2 to the pulled-back release position shown in FIG. 3, the instrument 10 has an actuating mechanism which is integrated in a hand grip 38 of the instrument 10 at the proximal end of the shaft 12.

This actuating mechanism comprises an actuating element 40 which is arranged in a blind bore 42 of the hand grip 38 extending transversely with respect to the longitudinal direction of the shaft 12.

The actuating element 40 is received in the blind bore 42 so as to be movable substantially transversely with respect to the longitudinal direction of the shaft 12 and thus with respect to the longitudinal direction of the tubular shaft 16, said actuating element 40 being operatively connected to the tubular shaft 16 in such a way that the tubular shaft 16 is moved from the locking position to the release position by means of a movement of the actuating element 40 from a first position shown in FIG. 2 to a second position shown in FIG. 3, and vice versa.

In the illustrative embodiment shown, the direction of movement of the actuating element 40 is perpendicular to the longitudinal direction of the shaft 12.

Figure 5:
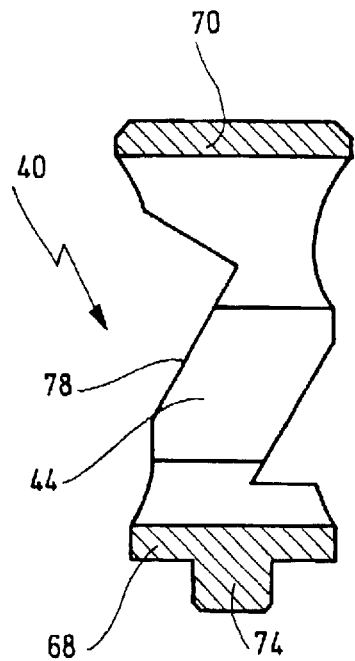
FIG. 5 shows, on an enlarged scale and in longitudinal section, a side view of an actuating element of the instrument in FIGS. 1 to 4.
Figure 6:
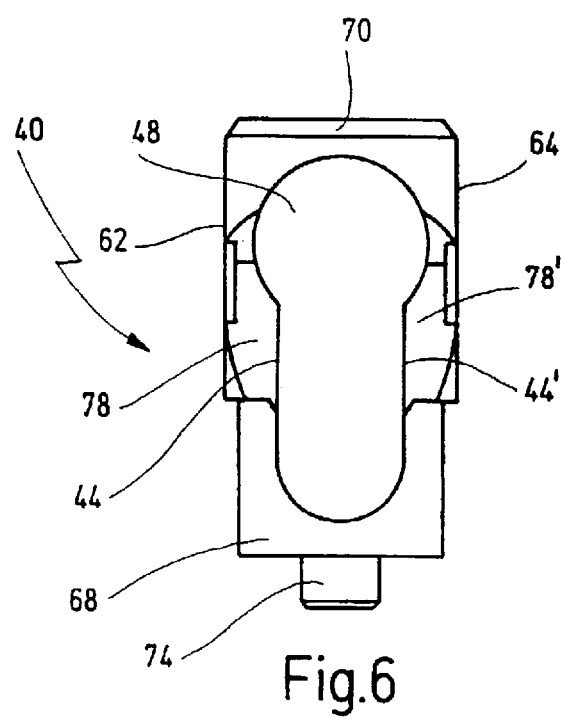
FIG. 6 shows the actuating element from FIG. 5 in a front view.

The actuating element, which is shown on an enlarged scale and in isolation in FIGS. 5 and 6, has for this purpose an engagement portion 44 which engages with a recess 46 on the tubular shaft 16 and is movable relative to the recess 46. The engagement portion 44 and the recess 46 are of such configuration that a movement of the actuating element 40 directed substantially transversely with respect to the longitudinal direction of the shaft 12 is converted into a longitudinal movement of the tubular shaft 16.

This aforementioned conversion of the movement of the actuating element 40 substantially transversely with respect to the longitudinal direction of the shaft 12 into a longitudinal movement of the tubular shaft 16 is achieved-by the fact that the engagement portion 44 and the recess 46 on the tubular shaft 16 extend obliquely with respect to the longitudinal direction of the shaft 12 and obliquely with respect to the direction of movement of the actuating element 40.

The actuating element 40 has in this case a total of two engagement portions 40 and 44' which at opposite circumferential positions of the tubular shaft 16 engage in corresponding recesses 46 of the tubular shaft. Both engagement portions 44 and 44' are shown in FIG. 6. The recesses 46 in the area of the proximal end of the tubular shaft 16 are formed by corresponding recesses in which the circumference of the tubular shaft 16 is reduced. Accordingly, the engagement portions 44 and 44' project radially inward to the extent that they can engage in the two recesses 46 on both sides of the tubular shaft 16.

According to FIG. 6, the actuating element 40 has an opening 48 which adjoins the two engagement portions 44 and 44' and whose clear diameter is slightly greater than the external diameter of the tubular shaft 16. The body of the actuating element 40 as a whole has a passage in the shape of a keyhole, as can be seen from FIG. 6. The portion of this keyhole formed as an oblong hole is bordered by the engagement portions 44 and 44', while the opening 48 forms the adjacent circular portion of the keyhole-shaped passage. The clear diameter of the oblong hole portion is accordingly smaller in the transverse direction than the external diameter of the tubular shaft 16 in the area outside the recesses 46.

The actuating element 40 can be moved from the second position shown in FIG. 3, in which the tubular shaft 16 is in its release position, to a third position in which the actuating element 40 completely disengages from the recess 46, the tubular shaft 16 being able to be removed from or mounted on the inner shaft 14 in the third position. In this third position of the actuating element 40, the opening 48 of the actuating element lies concentrically about the tubular shaft 16, while the engagement portions 44 and 44' disengage from the recesses 46 on the tubular shaft 16 and from the tubular shaft 16 as a whole.

Figure 7:
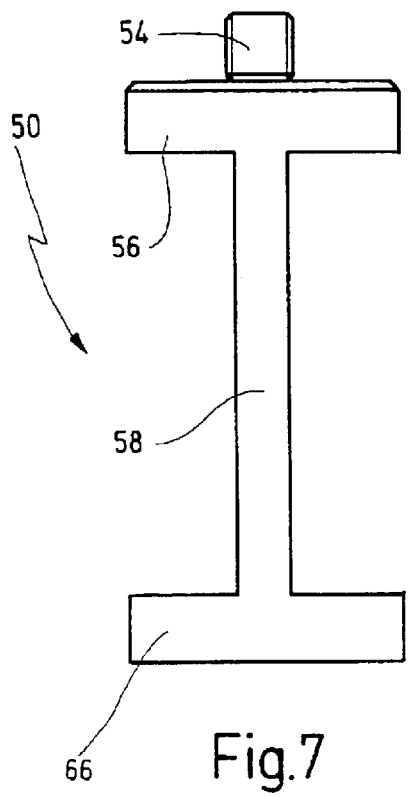
FIG. 7 shows, on an enlarged scale, a side view of a guide element of the instrument from FIGS. 1 to 4.
Figure 8:
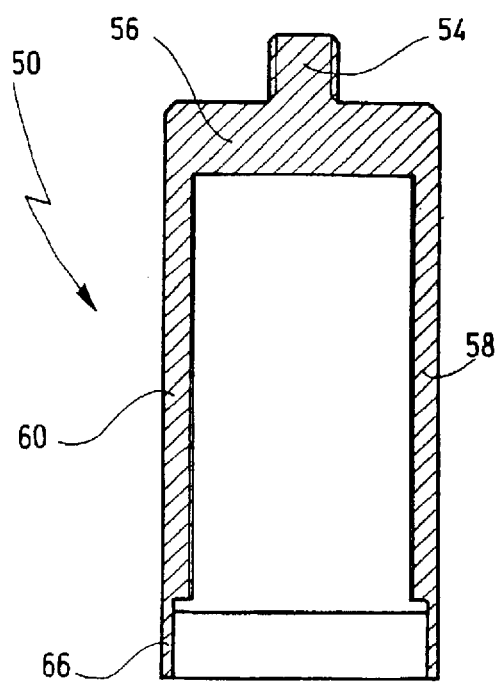
FIG. 8 shows the guide element from FIG. 7 in longitudinal section in a front view.

The actuating element 40 is moreover arranged in a guide element 50, which is shown in isolation in FIGS. 7 and 8.

The actuating element 40 is guided in a manner fixed against rotation in the guide element 50. However, the actuating element 40 is axially displaceable relative to the guide element 50, as will be described in more detail later.

The guide element 50 is securely connected to an operating element 52 in the form of a push button which can be operated with the thumb of the hand holding the hand grip 38. To secure the guide element 50 on the operating element 52, the guide element has, at its end directed toward the operating element 52, a stud 54 with an external thread via which the guide element 50 can be screwed into the operating element 52.

At its end toward the stud 54, the guide element 50 has a plate 56 from whose outer periphery two narrow webs 58 and 60 extend which lie diametrically opposite one another. The two webs 58 and 60 serve to rotationally secure and axially guide the actuating element 40, which is equipped with corresponding grooves 62 and 64 (FIG. 6). The guide element 50 is itself displaceably guided and fixed against rotation in the blind bore 42.

At their end opposite the plate 56, the webs 58 and 60 are connected to a ring 66 which has a clear internal diameter which is slightly greater than an external diameter of a plate 68 of the actuating element 40.

The actuating element 40 bears with a further plate 70, opposite the plate 68, against the plate 56 of the guide element 50. When the operating element 52 is pressed down, the actuating element 40 is thus entrained in its direction of movement transverse to the shaft 12 by the guide element 50, which is securely connected to the operating element 52.

The actuating element 40 is further supported against a first spring 72. The first spring 72 is in this case arranged between a base of the blind bore 42 and a stud 74 extending from the plate 68 of the actuating element 40. The first spring 72 is plugged onto the stud 74.

A second spring 76 is also provided which is arranged underneath the ring 66 of the guide element 50 and connected to the latter. The second spring has a clear internal diameter which is greater than the external circumference of the actuating element 40, or, to be more exact, greater than the external circumference of the plate 68 of the actuating element 40, so that the plate 68 can move down into the second spring 76, as will be described later.

Moreover, the second spring 76 is harder than the first spring 72.

The second spring 76, which is connected to the guide element 50, is at a distance from the base of the blind bore 42 in the first position of the actuating element 40 and only comes into contact with the base of the blind bore 42 when the actuating element 40 is in the second position shown in FIG. 3. Thus, the actuating element 40 can be moved from the position shown in FIG. 2 to the position shown in FIG. 3 counter to the force of the first spring 72 alone, and it is only when moving from the second position shown in FIG. 3 to the third position according to FIG. 4 that it must additionally be moved counter to the force of the second spring 76.

The function of the instrument 10 for changing the tool 18 is now described below.

In FIG. 2, the instrument 10 is shown in a state in which the tool 18 is arranged locked on the shaft 12. In this state, the actuating element 40 is located in its first position, into which the actuating element 40 is prestressed, specifically by the action of the first spring 72.

Starting from the position shown in FIG. 2, the operating element 52 in the form of the push button can now be pressed down transversely with respect to the longitudinal direction of the shaft 12 until the second position of the actuating element 40, shown in FIG. 3, is reached. This position of the actuating element 40 is made noticeable to the person using the instrument 10 by virtue of the fact that the second spring 76 now comes to bear against the base of the blind bore 42 and forms a kind of limit stop which is made noticeable by the greater resistance of the second spring 76, becoming now additionally active.

During the movement of the actuating element 40 from the first position shown in FIG. 2 to the second position shown in FIG. 3, the engagement portions 44 and 44' of the actuating element 40 slide in the recesses 46 of the tubular shaft 16, as a result of which a forced guiding of the tubular shaft 16 is obtained in such a way that the tubular shaft 16 is moved in the proximal direction into the pulled-back release position shown in FIG. 3. In this release position, the transversely extending portion 26 of the holder 24 of the tool 18 disengages from the recess 34 of the tubular shaft 16, so that the portion 26 of the holder 24 can now be turned 90° counterclockwise in the bayonet-like recess 28 and finally pulled out of the recess 28.

To fit a new tool as a replacement for the tool 18, the reverse procedure is followed, i.e. while the actuating element 40 is being held in the second position by pressure exerted on the operating element 52 in the second position according to FIG. 3, a new tool can be inserted into the bayonet-like recess 28 and can be turned 90° clockwise, after which the press button 52 is let go and the actuating element 40, by means of its engagement portions 44 and 44' engaging in the recesses 46 of the tubular shaft, automatically pushes the latter forward again into the pushed-forward locking position shown in FIG. 2. In the second position of the actuating element 40, the engagement portions 44 and 44' remain engaged with the recesses 46. Because of the prestressing of the actuating element 40 in the first position shown in FIG. 2 the tool is fixed to the shaft.

Starting from the second position of the actuating element 40 shown in FIG. 3, said actuating element 40 can be moved further into the third position shown in FIG. 4 by means of the operating element 52 being pressed further down, the actuating element 40 now having to be moved both counter to the force of the first spring 72 and also additionally counter to the force of the second spring 76. The operating element 52 is fully depressed when the tubular shaft 16 is to be removed from the inner shaft 14. In the third position shown in FIG. 4, the engagement portions 44 and 44' of the actuating element 40 completely disengage from the recesses 46 on the tubular shaft, while the opening 48 of the actuating element 40 now comes to lie concentrically with respect to the tubular shaft 16, so that the tubular shaft can be pulled out from the actuating element 40 and thus completely removed from the inner shaft 14. To do so, the tool 18 was removed beforehand from the shaft 12 in accordance with FIG. 3. The tubular shaft 16, the inner shaft 14 with the hand grip 38, and the tool 18 can now be separately cleaned.

To fit the tubular shaft 16 on the inner shaft 14 and connect the tubular shaft 16 to the hand grip 38, however, it is no longer necessary for the operating element 52 to be pressed down to the maximum extent counter to the force of both springs 72 and 76, as is shown in FIG. 4, and instead, because of a further embodiment of the instrument 10, the operating element 52 does not have to be activated.

Figure 9:
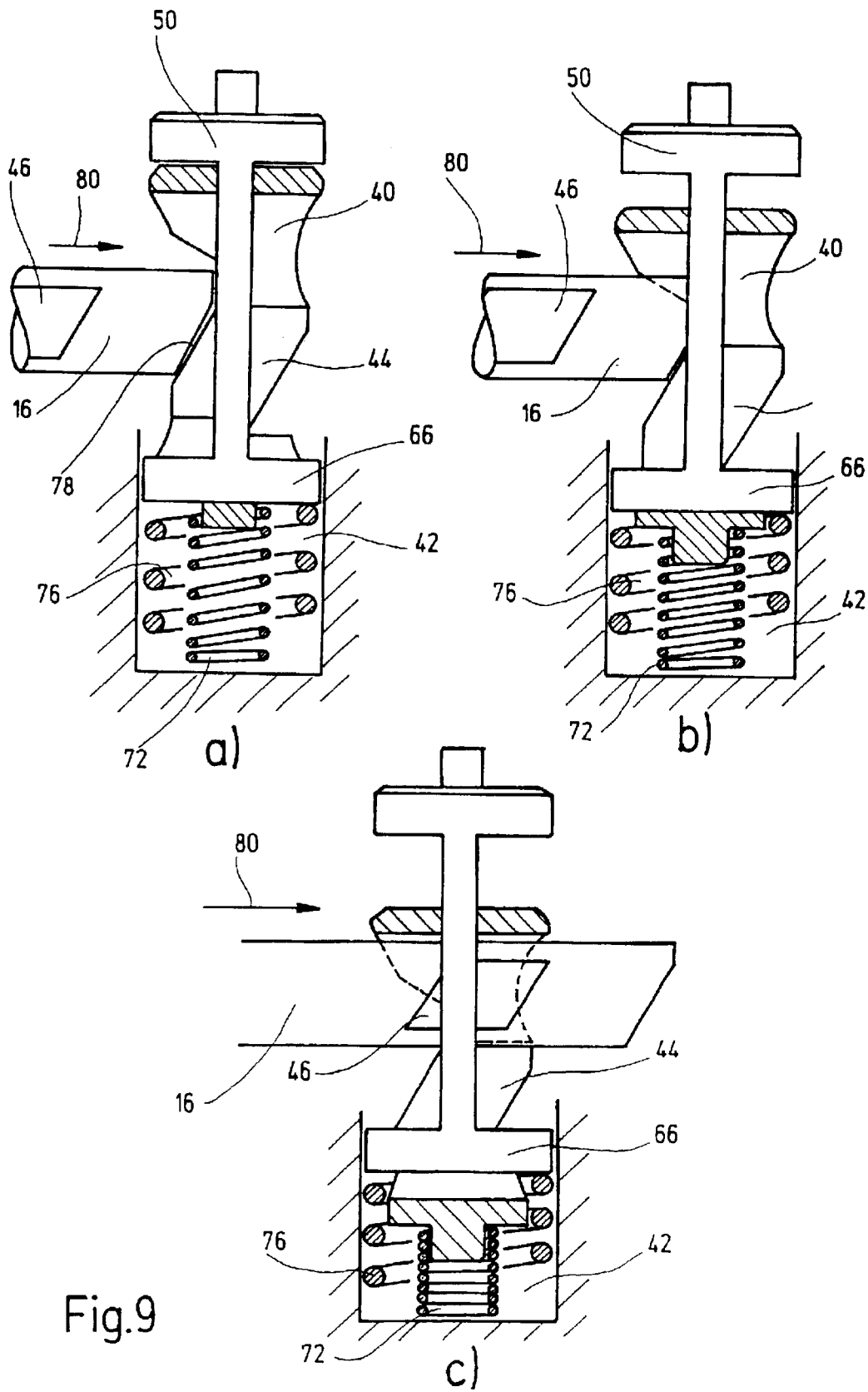
FIGS. 9a) to c) are a diagrammatic representation of the procedure for fitting the tubular shaft on the instrument in three separate views showing the instrument cut away in the area of the actuating element.

This is because the actuating element 40 has an abutment bevel 78 on the distal side, against which abutment bevel 78 the proximal end of the tubular shaft comes to bear when the tubular shaft 16 is pushed onto the inner shaft 14, as is shown in FIG. 9a).

According to FIG. 6, the actuating element 40 has such abutment bevels 78 and 78' on the distal side of each of its two engagement portions 44 and 44'.

By pushing the tubular shaft 16 farther back according to FIG. 9b), the actuating element 40 is now moved from its first position, into which the actuating element 40 is prestressed by the first spring 72, into the second position and via the latter into the third position according to FIG. 9c), without the operating element 52 and the guide element 50 connected to it being moved. This is made possible by the fact that the actuating element 40 is movable relative to the guide element 50, and the outer circumference of the actuating element 40 is smaller than the clear internal diameter of the ring 66 of the guide element 50 and also less than the clear internal diameter of the second spring 76. To fit the tubular shaft 16 on the inner shaft 14, the actuating element 40 must therefore be moved from its first position to the third position counter to the force of the first spring 72 alone and thus counter to a weaker force into the third position, this force being applied by displacement of the tubular shaft 16 in the proximal direction.

Starting from FIG. 9c), the tubular shaft 16 must only be displaced a small distance farther proximally in the direction of an arrow 80 until the recess 46 and the engagement portions 44 and 44' are flush with one another, and the engagement portions 44 and 44' in this position automatically latch in the recesses 46 on the tubular shaft 16 because of the prestressing by the first spring 72.

It will be evident from what has been described above that the instrument 10 has an actuating mechanism with a two-stage latch, of which the first movement stage serves for changing the tool 18, and of which the second stage serves for removal of the tubular shaft 16 from the inner shaft 14. Moreover, the actuating element 40 is uncoupled from the operating element 52 such that in order to fit the tubular shaft 16 on the inner shaft 14, the operating element 52 is not actuated, but instead the tubular shaft simply has to be pushed on, as a result of which an automatically acting latching mechanism is created.

What is claimed is:

1. A medical instrument, comprising: a shaft having an extension in a longitudinal direction, and further having a distal end, said shaft further having an inner shaft and a tubular shaft surrounding said inner shaft and being displaceable relative thereto; a tool mounted on said distal end of said shaft in such a way as to be removable therefrom, said tool being locked on said shaft when said tubular shaft is in a locking position and being removable from said shaft when said tubular shaft is in a release position relative to said inner shaft; and an actuating element movable substantially transversely with respect to said longitudinal direction of said tubular shaft and connected operatively to said tubular shaft in such a way that said tubular shaft is moved from said locking position to said release position by moving said actuating element from a first position to a second position, and vice versa.

2. The instrument of claim 1, wherein said actuating element has an engagement portion which engages with a recess on said tubular shaft and is movable relative to said recess, said engagement portion and said recess having such a configuration that a movement of said actuating element directed substantially transversely with respect to said longitudinal direction is converted into a movement of said tubular shaft in said longitudinal direction.

3. The instrument of claim 2, wherein said engagement portion and said recess extend obliquely with respect to said longitudinal direction of said shaft and obliquely with respect to a direction of movement of said actuating element.

4. The instrument of claim 1, wherein said actuating element can be moved from said second position to a third position in which said actuating element completely disengages from said recess, and said tubular shaft can be removed from said inner shaft.

5. The instrument of claim 1, wherein said actuating element is prestressed into said first position.

6. The instrument of claim 1, wherein said actuating element can be moved from said second position to a third position in which said actuating element completely disengages from said recess, and said tubular shaft can be removed from said inner shaft, and wherein said actuating element is prestressed into said first position, and wherein, in order to fit tubular shaft on said inner shaft, said actuating element can be moved into said third position counter to said first force alone.

7. The instrument of claim 1, wherein said actuating element has two engagement portions which engage, at opposite circumferential positions of said tubular shaft, in corresponding recesses of said tubular shaft.

8. The instrument of claim 1, wherein said actuating element has an opening which adjoins said engagement portion and whose clear diameter is greater than an external diameter of said tubular shaft.

9. The instrument of claim 1, wherein said actuating element is supported against a first spring.

10. The instrument of claim 1, wherein said actuating element is guided in a guide element which is connected to an operating element in form of a push button, in such a way that, by pressing said operating element, said guide element entrains said actuating element.

11. The instrument of claim 10, wherein said actuating element is displaceable relative to said guide element.

12. The instrument of claim 1, wherein said actuating element is supported against a first spring, and wherein said actuating element is guided in a guide element which is connected to an operating element in form of a push button, in such a way that, by pressing said operating element, said guide element entrains said actuating element, and wherein said actuating element, additionally supported against a second spring, can be moved from said second position to said third position.

13. The instrument of claim 12, wherein said second spring is supported against said guide element and only upon movement of said actuating element from said second position to said third position said second spring is made active for removing said tubular shaft.

14. The instrument of claim 1, wherein said actuating element is supported against a first spring, and wherein said actuating element is guided in a guide element which is connected to an operating element in form of a push button, in such a way that, by pressing said operating element, said guide element entrains said actuating element, and wherein said actuating element, additionally supported against a second spring, can be moved from said second position to said third position, and wherein a clear internal diameter of said second spring is greater than an external circumference of said actuating element, said first spring being arranged inside said second spring.

15. The instrument of claim 1, wherein said actuating element is supported against a first spring, and wherein said actuating element is guided in a guide element which is connected to an operating element in form of a push button, in such a way that, by pressing said operating element, said guide element entrains said actuating element, and wherein said actuating element, additionally supported against a second spring, can be moved from said second position to said third position, and wherein said second spring is harder than said first spring.

16. The instrument of claim 1, wherein an abutment bevel for a proximal end of said tubular shaft is formed on a distal side of said actuating element so that said actuating element is moved into said third position when said proximal end runs onto said abutment bevel.

17. The instrument of claim 1, wherein said actuating element is arranged to be operated on a handgrip of said instrument.

18. The instrument of claim 1, wherein said tubular shaft is pushed forward relative to said inner shaft in said locking position and is pulled back in said release position.

19. The instrument of claim 1, wherein said tool is an electrode for coagulation or cutting of tissue.

20. A medical instrument, comprising: a shaft having an extension in a longitudinal direction, and further having a distal end, said shaft further having an inner shaft and a tubular shaft surrounding said inner shaft and being displaceable relative thereto; a tool mounted on said distal end of said shaft in such a way as to be removable therefrom, said tool being locked on said shaft when said tubular shaft is in a locking position and being removable from said shaft when said tubular shaft is in a release position relative to said inner shaft; and an actuating element movable substantially transversely with respect to said longitudinal direction of said tubular shaft and connected operatively to said tubular shaft in such a way that said tubular shaft is moved from said locking position to said release position by moving said actuating element from a first position to a second position, and vice versa, wherein said actuating element can be moved from said second position to a third position in which said actuating element completely disengages from said recess, and said tubular shaft can be removed from said inner shaft, and wherein said actuating element is prestressed into said first position, and wherein said actuating element can be moved from said first position to said second position counter to a first force and, in order to remove said tubular shaft from said inner shaft, can be moved from said second position to said third position counter to a second force which is greater than said first force.

21. A medical instrument, comprising: a shaft having an extension in a longitudinal direction, and further having a distal end, said shaft further having an inner shaft and a tubular shaft surrounding said inner shaft and being displaceable relative thereto; a tool mounted on said distal end of said shaft in such a way as to be removable therefrom, said tool being locked on said shaft when said tubular shaft is in a locking position and being removable from said shaft when said tubular shaft is in a release position relative to said inner shaft; and an actuating element movable substantially transversely with respect to said longitudinal direction of said tubular shaft and connected operatively to said tubular shaft in such a way that said tubular shaft is moved from said locking position to said release position by moving said actuating element from a first position to a second position, and vice versa, wherein a distal end of said inner shaft has a bayonet-like recess with a portion which initially extends axially and then partially circumferentially, a holder being arranged at a proximal end of said tool, which holder can be inserted with a transversely extending portion into said bayonet-like recess, and at least one axial recess being formed on said tubular shaft, into which axial recess said transversely extending portion of said holder engages in said locking position of said tubular shaft.

* * * * *